(12) United States Patent
Kulås et al.

(10) Patent No.: US 6,528,669 B1
(45) Date of Patent: Mar. 4, 2003

(54) RECOVERY OF POLYUNSATURATED FATTY ACIDS FROM UREA ADDUCTS

(75) Inventors: Elin Kulås, Langesund (NO); Harald Breivik, Porsgrunn (NO)

(73) Assignee: Norsk Hydro ASA, Oslo (NO)

( * ) Notice: Subject to any disclaimer, the term of this patent is extended or adjusted under 35 U.S.C. 154(b) by 0 days.

(21) Appl. No.: 10/031,712

(22) PCT Filed: Jul. 31, 2000

(86) PCT No.: PCT/NO00/00252

§ 371 (c)(1),
(2), (4) Date: Apr. 3, 2002

(87) PCT Pub. No.: WO01/10809

PCT Pub. Date: Feb. 15, 2001

(30) Foreign Application Priority Data

Aug. 11, 1999 (NO) .................................................. 993882

(51) Int. Cl.$^7$ .................................................. C11B 7/00
(52) U.S. Cl. ........................ 554/186; 554/184; 554/185; 554/205
(58) Field of Search ................................. 584/184, 185, 584/186, 205

(56) References Cited

FOREIGN PATENT DOCUMENTS

JP        10/095744       *   4/1998

OTHER PUBLICATIONS

Nillsson et al., JAOCS, vol. 66, No. 11, pp. 1596–1600, 1989.*
William Nilsson, et al., "Supercritical Fluid Fractionation of Fish Oil Esters Using Incremental Pressure Programming and a Temperature Gradient" JACOCS, 1989, vol. 66, No. 11, pp. 1596–1600.
M. Alkio, et al., "Purification of Polyunsaturated Fatty Acid Esters from Tuna Oil with Supercritical Fluid Chromatography," JAOCS, 2000, vol. 77, No. 3, pp. 3, pp. 315–321 (1989).

* cited by examiner

Primary Examiner—Deborah D. Carr
(74) Attorney, Agent, or Firm—Fitzpatrick, Cella, Harper & Scinto

(57) ABSTRACT

Polyunsaturated fatty acids, as free fatty acids, fatty acid esters or fatty acid amides, especially EPA and/or DHA, DPC 9/02, are recovered from urea adducts, such as obtained as by-products in the processing of fish and other oils, by treatment with a subcritical or supercritical fluid.

21 Claims, No Drawings

RECOVERY OF POLYUNSATURATED FATTY ACIDS FROM UREA ADDUCTS

This application is a 371 of PCT/No.00/00252 filed Jul. 31, 2000.

This invention relates to a method for recovering polyunsaturated fatty acids from urea adducts with mixed saturated and unsaturated fatty acids or esters or amides. The invention has particular, although not exclusive, application to the recovery of polyunsaturated fatty acids from urea adducts formed during commercial processes for concentrating such acids from fish and vegetable oils.

In this specification and claims the term "fatty acid" is used in the sense that the fatty acid may be in the form of the free fatty acid or a fatty acid ester, especially esters with $C_1$–$C_4$ alcohols, or a fatty acid amide. The same applies when any fatty acid is discussed using its proper name or an abbreviation thereof, such as for instance eicosapentaenoic acid (EPA) and docosahexaenoic acid (DHA).

It has been known for many years that urea forms complexes with organic compounds with long straight chains of carbon atoms, and moreover that the amount of urea required for such complex formation increases proportionately with the carbon chain length (Marschner, "The Story of Urea Complexes", Chemical & Engineering News, 33, No. 6, Feb. 7, 1955, pps 494–6). Such urea adduct formation is employed industrially to separate wanted from unwanted components in the recovery of omega-3 polyunsaturated fatty acids, or mixtures thereof, from fish oils, as described by Breivik et al in the paper "Production and Quality Control of n-3 Fatty Acids" in "Fish, Fish Oil and Human Health", published by W. Zuckschwerdt Verlag GmbH, Munich, 1992.

There is a growing demand for polyunsaturated omega-3 fatty acids and fatty acid mixtures, particularly for EPA and DHA which are increasingly being shown to play an important role in human and animal health and well-being. Commercially, compositions with high concentrations of EPA and/or DHA are obtained from fish oils. Partially processed fish oils which contain relatively high concentrations of EPA and DHA (up to about 30% EPA+DHA) are commercially available, but these oils contain many other similarly long chain unsaturated (mono- and poly-) and saturated fatty acids, and further complex and costly processing is necessary in order to recover EPA and DHA in desired concentrations, which depend on the intended use but which may typically vary from about 50% EPA+DHA for a health supplement up to 90% or higher EPA+DHA for pharmaceutical use. In some cases substantially pure EPA and/or DHA are needed.

At the same time as the demand for purified fish oil products such as concentrates of EPA and DHA is growing so the supply of partially processed fish oil containing relatively high concentrations of EPA and DHA is becoming increasingly scarce and hence more costly. There is thus a general need to ensure that the desired components eg EPA and DHA are recovered from the raw material to the greatest extent possible, and that wastage of these valuable fatty acids should be minimised. It would also be desirable to reduce the high cost of purifying fish oils.

As already mentioned, urea fractionation is used commercially in the processing of fish oils to recover desired omega-3 fatty acids. In a typical process the fish oil is first hydrolysed to convert the glycerides to fatty acids or transesterified, most often with ethanol, to form fatty acid esters. A processing step which removes short chain fatty acids or esters, commonly molecular distillation, may then be employed. Either before, but more usually after, the molecular distillation step, a urea fractionation is performed to further increase the concentration of the desired long chain polyunsaturated fatty acids. Stepwise urea fractionation may be carried out where the product from a first fractionation is used as feed in a second or further fractionation. Subsequently, molecular distillation, bleaching and/or chromatography, or other processing, is often employed in order to produce a product with the desired qualities.

Urea fractionation may also be employed to increase the concentration of polyunsaturated fatty acids from certain vegetable oils, for instance in a process for recovering γ-linolenic acid in high concentration from evening primrose oil, borage oil or blackcurrant seed oil (see eg "Fractionation of Blackcurrant Seed Oil" by Traitler et al, JAOCS, 65, No. 5, May 1988).

In a typical commercial plant for manufacturing concentrated omega-3 fatty acids from fish oil the urea fractionation serves to increase the total EPA+DHA concentration from about 50% to about 80% by weight. The urea adduct which precipitates out contains a significant concentration, typically about 25–30% by weight, of fatty acids although the precise composition is highly dependent on where the urea fractionation is-employed in the manufacturing process. These fatty acids, which may be in free acid form or in the form of esters, are mainly saturated or monounsaturated fatty acids but they also include significant amounts of polyunsaturated fatty acids as well, typically up to 30–40% by weight of-the fatty acid fraction in the adduct. Currently, this urea adduct is treated as a by-product of the refining process, which may be used as an agricultural fertilizer, but in view of the growing scarcity and increasing expense of fish oils, and of the high cost of processing them, it would be desirable to be able to recover the valuable polyunsaturated fatty acids from the urea adduct in an economically worthwhile manner. Such a process would also desirably permit the recovery of the urea in a condition suitable for direct recycling.

It is known that urea adducts with fatty acids decompose when heated to about 130° C. or more. The freed fatty acids form a distinct layer in the separation vessel above the molten urea, and these two layers are readily separated. However, heating the urea adduct above 130° C. is liable to cause oxidation and decomposition of the polyunsaturated fatty acids, while urea itself is also somewhat unstable at high temperatures and may form by-products such as biuret. In any case, the concentration of polyunsaturated fatty acid in the fatty acid fraction which is recovered is only the same as the concentration of these fatty acids in the urea adduct. Moreover, the separated urea requires regranulation before it can be recycled to the urea fractionation step.

It is also known to recover the bound fatty acids from the urea adducts by heating with non-polar solvents, e.g. hydrocarbons such as isooctane. The fatty acids are extracted by the solvent, and can then be recovered by distillation of the solvent. However, this process involves use of very large quantities of solvent, which would not be acceptable on the commercial scale, and moreover does not lead to the direct recovery of the wanted fatty acids e.g. EPA and DHA. The urea itself becomes contaminated with the solvent, which means that a solvent removal step must be included if the urea is to be recycled, and the fatty acid fraction also may contain traces of the solvent which for many purposes would be unacceptable.

There thus is currently no simple, economically attractive process available for recovering desired polyunsaturated fatty acids from the urea adducts.

It is known to use supercritical fluids as selective solvents in various extractive processes. A supercritical fluid is a compound which under normal atmospheric conditions may be either a liquid or a gas but which above a critical temperature and pressure has a density comparable to that of a liquid while exhibiting a diffusivity, that is transport properties, of a gas. This combination of properties results in a fluid with good solvent properties which moreover can be varied over a wide range by varying the pressure and temperature of the supercritical fluid. Carbon dioxide is widely used as a supercritical fluid as its critical temperature and pressure (31° C., 74 bar) permit processing under acceptable conditions, and it is inert, non-toxic and cheaply and readily available.

It has been shown that the urea fractionation itself can be performed using supercritical $CO_2$ as a solvent. Such a process is described in JP-A-60214757. When treating a fatty acid mixture with urea using supercritical $CO_2$ as solvent, the urea and urea adducts formed are only sparingly soluble in the $CO_2$ while the polyunsaturated fatty acids remain dissolved in the supercritical fluid and can be recovered by decompression. Arai et al in a paper entitled "Fractionation of Fatty Acids and their Derivatives by Extractive Crystallization Using Supercritical Gas as a Solvent" in World Congress III of Chemical Engineering, Tokyo, Vol. II, 7a-304, pp 152–155, 1986, describe a method for fractionating fatty acids on the basis of their degree of unsaturation by means of extractive crystallization with urea in supercritical $CO_2$. These authors postulate an industrial separation process in which the supercritical fluid saturated with the fatty acids to be fractionated and fine powder of urea are subjected to countercurrent contact in a tower. The unsaturated components preferentially remain dissolved in the supercritical phase, whilst the saturated acids preferentially form an adduct with the urea from which they can be subsequently recovered by thermal decomposition. Such a process, of course, is not useful for recovering polyunsaturated fatty acids from already-formed urea adducts.

We have now found, in accordance with the present invention, that long chain polyunsaturated fatty acids such as EPA and DHA can be preferentially extracted from an urea adduct containing saturated, mono-unsaturated and polyunsaturated fatty acids, such as is obtained as a by-product in the processing of fish oils, by treating the urea adduct with a supercritical fluid such as $CO_2$ at a temperature not above 70° C. This result is highly surprising since in general the solubility of compounds of similar polarity in supercritical fluids decreases with increasing molecular weight or chain length, and indeed in accordance with this general rule the commercially valuable long chain polyunsaturated fatty acids such as EPA and DHA are less soluble in supercritical $CO_2$ than the more saturated, shorter chain fatty acids which are present in the urea adduct. See "Supercritical Fluid Technology in Oil and Liquid Chemistry", AOCS Press, Champion, Ill., 1996, page 180 et seq. Although not wishing to be bound by theory, one possible explanation for our discovery that the polyunsaturated fatty acids are preferentially extracted from the urea adduct by the supercritical fluid could be that these fatty acids form weaker adducts with urea than do the shorter-chain saturated fatty acids.

The present invention broadly provides a method for recovering polyunsaturated fatty acids from an urea adduct containing saturated and/or monounsaturated fatty acids in addition to polyunsaturated fatty acids, which method comprises the steps of subjecting said urea adduct to extraction treatment with a subcritical or supercritical fluid at a temperature not above 70° C., and recovering from said supercritical fluid a fatty acid fraction enriched in said polyunsaturated fatty-acids. Preferably, the extraction treatment is conducted at a temperature of from 40°–55° C.

The method of the invention, in preferred embodiments, permits the recovery of a fatty acid fraction from an urea adduct, obtained as a by-product in the processing of fish oil to make concentrated EPA and/or DHA compositions, which contains 50% or more, typically 60–65%, of EPA plus DHA. This recovered fraction may advantageously be recycled to the fish oil processing system, to reduce the losses of the valuable EPA and DHA components caused by the urea fractionation step, and since the recovered fraction itself contains quite high concentrations of EPA and DHA it may be returned to the system at a relatively upstream point, i.e. avoiding some of the early but costly purification steps, thereby enhancing even more the cost benefits which can be gained.

It is noteworthy that the urea adduct from the second or later stages in a stepwise urea fractionation is especially rich in the desired long chain polyunsaturated fatty acids, EPA and DHA. Consequently, it is a particular advantage of the invention that it permits the ready recovery of these valuable fatty acids.

As previously indicated, the urea adducts obtained in the commercial manufacture of concentrated omega-3 fatty acids from fish oil contain the bound fatty acids either as free acids or as esters, particularly ethyl esters. Accordingly, the fatty acid fractions which are recovered in the practice of the preferred embodiments of the present invention will likewise contain the fatty acids either as free acids or as esters. It is also considered likely that the present invention may be useful if the fatty acids are contained as amides. In the present specification, therefore, it is to be understood that references to recovering polyunsaturated fatty acids or fatty acid fractions are intended to include the recovery of the acids in the form of esters or amides as well as in free acid form.

The urea adduct residue remaining after the extraction with subcritical supercritical fluid at not more than 70° C. may if desired be disposed of as hitherto, e.g. as an agricultural fertilizer, but preferably is itself subjected to further extraction with supercritical fluid at a temperature of from 65°–130° C., preferably from 70°–110° C., in order to recover a second fatty acid fraction. This second extraction step can be operated to remove a substantial proportion of the fatty acid remaining in the urea adduct, and although the second fatty acid fraction which results is not enriched in the valuable polyunsaturated fatty acids nonetheless it is desirably recycled to the fish oil processing system at a downstream point in order to help the overall economics of the system. Alternatively, this second fatty acid fraction can be hydrogenated and used in the manufacture of, for instance, detergents.

It is preferred to use a supercritical fluid, and especially supercritical $CO_2$ in both extraction steps. As previously mentioned, $CO_2$ is inert and non-toxic, and therefore is particularly desirable for use in the preparation of products to be used as food supplements or as pharmaceuticals. However, other supercritical fluids can be used, for instance $N_2O$ and ethane.

As is known to those skilled in the art, the solvent properties of supercritical fluids such as $CO_2$ can be modified by the addition of cosolvents. Thus, the addition of polar solvents such as ethanol and acetone generally increases the solubility with regard to polar compounds. Although the use of cosolvents is possible in the extraction method of the present invention, we have so far found that it seems to confer little or no advantage. Indeed, in experiments using ethanol as cosolvent we found that there was a tendency for urea to precipitate in the valves of the equipment, which made the process more difficult to perform. Nonetheless, there may be situations where the use of a cosolvent is beneficial.

The treatment of the urea adduct with the supercritical fluid may be carried out, for example, by passing the supercritical fluid through the urea adduct to be treated placed in an extraction vessel, and then the supercritical fluid containing extracted fatty acids is expanded into the gas phase in a separation vessel, whereby the fatty acid fraction is recovered. The released gas can then be recycled.

The first, essential, extraction step with supercritical fluid is conducted, as previously noted, at a temperature not in excess of 70° C. The minimum temperature for this extraction is the critical temperature of the supercritical fluid employed, i.e. 31° C. in the case of $CO_2$. However, in this first extraction step it is also possible to use a subcritical fluid e.g. in the case of $CO_2$ it is possible to employ a temperature below 31° C., when the supercritical $CO_2$ is transformed into liquid $CO_2$. As the temperature used rises, the overall recovery of polyunsaturated fatty acids such as EPA and DHA increases but the proportion of these desired polyunsaturated fatty acids in the extracted fatty acid fraction starts to decrease. It appears that the optimum extraction temperature, taking both factors into account, ranges from 40°–55° C.

In the second, optional but preferred, extraction step with supercritical fluid, the temperature is from 65°–130° C. Whilst the use of a relatively high temperature promotes release of fatty acids from the urea adduct, as the strength of the bonds in the adduct decreases with increasing temperature, on the other hand increasing the temperature at a constant pressure causes a reduction in the density of the supercritical fluid, and thus also a reduction in the solubility of the fatty acids in the supercritical fluid. Accordingly, it is generally preferred that the optional extraction be carried out at from 70°–110° C. in order to cause adequate weakening of the urea-fatty acid adducts while maintaining a relatively high fatty acid solubility in the supercritical $CO_2$. The temperature must not exceed 130° C. since above this temperature the urea adduct begins to melt, thus preventing further extraction of fatty acids.

At a given temperature, the density of a supercritical fluid such as $CO_2$, and consequently the solubility of fatty acids, will increase with increased pressure. Consequently, it is preferred to conduct the extraction steps at relatively high pressures, preferably at from 200–300 bar in the case of $CO_2$.

The flow rate of the supercritical fluid over the urea adduct appears not to be critical. Accordingly, a flow rate is generally selected which is appropriate to the equipment which is used.

The urea adduct which remains after the second, optional extraction with supercritical fluid, i.e. at 65° C. or above, is considerably depleted of its original fatty acid content. Nonetheless, our preliminary findings are that if this urea is recycled to the urea fractionating step of a fish oil processing system then, surprisingly, there is an increase in the concentration of EPA and DHA in the product which is obtained. This advantageous effect may possibly be due to the fact that the regenerated urea adduct, unlike urea itself, is in a crystalline form which dissolves more easily in the solvent which is used to form an urea solution in the urea fractionation process. The fact that the regenerated urea adduct dissolves easily in the solvent also means that less solvent need be used in the fractionation process, which of course helps reduce costs.

The method of the present invention may be carried out in a conventional supercritical fluid extraction apparatus. Typically, liquefied solvent is pressurised by a pump and brought to the operating temperature in a heat exchanger. The treatment of the urea adduct is then carried out by contacting the urea adduct packed in the extraction vessel with the supercritical fluid as this is passed through the vessel. The long chain polyunsaturated fatty acids or esters in the adduct are preferentially dissolved in the supercritical fluid, to leave the adduct with depleted concentrations of these fatty acids. The supercritical fluid effluent from the extraction vessel is then depressurised in a separation vessel, normally to a pressure below the critical pressure of the solvent. The fatty acids are then no longer soluble and may be continuously recovered from the separation vessel. The released gas can be recycled.

The invention is illustrated by the Examples which follow.

In the Examples, the amount of fat in the urea adduct before and after treatment with supercritical $CO_2$ was calculated from the results of the determination of total nitrogen in the samples. To determine the fatty acid composition of the urea adduct, the adduct was dissolved in hydrochloric acid and the fatty acid ethyl esters was recovered by extraction with isooctane. The organic phase was analysed directly by gas chromatography.

A stainless steel extraction cylinder was filled with urea adduct and placed in the extraction vessel. $CO_2$ from a gas cylinder was liquefied in a condenser at 2° C., pressurised by a membrane pump and brought to the desired temperature in a heat exchanger. Supercritical $CO_2$ was passed through the urea adduct and subsequently expanded to 50 bar in a separation vessel heated to 50° C., which rendered the fatty acid ethyl esters insoluble in the $CO_2$ gas. The fatty acid extract was recovered from the separation vessel by further expansion to atmosphere. $CO_2$ was recycled. The concentration of EPA and DHA in the product was determined by gas chromatography.

The urea adduct starting material used in Examples 1 and 2 and Comparative Example 1 contained 27% fat, as ethyl esters, and 73% urea. The concentration of EPA+DHA in the fat was 40%, the rest being saturated, monounsaturated and a small amount of other polyunsaturated fatty acids.

EXAMPLE 1

Step 1: Urea adduct (80 g) was treated with supercritical $CO_2$ at 250 bar and 40° C. for 30 min. $CO_2$ flow rate was 0.7 kg/hr. 1.6 g fatty acid ethyl esters were extracted (7.4% of theoretical yield of fat). The concentration of EPA+DHA was 62%.

Step 2: The treated urea adduct from step 1 was treated further with supercritical $CO_2$ at 250 bar and 75° C. for 3 hrs. The $CO_2$ flow rate was 0.7 kg/hr. 12 g fatty acid ethyl esters were extracted (56% of theoretical yield of fat). The concentration of EPA+DHA in the product was 39%. The residual amount of fat in the urea adduct was 5%.

EXAMPLE 2

Step 1: Urea adduct (80 g) was treated with supercritical $CO_2$ at 300 bar and 50° C. for 30 min. $CO_2$ flow rate was 2.0 kg/hr. 5.7 g fatty acid ethyl esters were extracted (27% of theoretical yield of fat).

The concentration of EPA+DHA in the product was 62%.

Step 2: The urea adduct from Step 1 was treated further with supercritical $CO_2$ at 300 bar and 75° C. for 2 hrs. The $CO_2$ flow rate was 2.0 kg/hr. 9.6 g fatty acid ethyl esters were extracted (44% of theoretical yield of fat). The concentration of EPA+DHA in the product was 29%. The residual amount of fat in the urea adduct was 2%.

COMPARATIVE EXAMPLE 1

Urea adduct (80 g) was treated with supercritical $CO_2$ at 300 bar and 75° C. for 2.5 hours. The $CO_2$ flow rate was 2.0 kg/hr. 16.8 g fatty acid esters were extracted (78% of theoretical yield of fat). The concentration of EPA+DHA was 41% i.e. there was no material enrichment of the fatty acid fraction which was recovered.

This Comparative Example shows that a high temperature in the first extraction step confers no advantage.

EXAMPLE 3

This example illustrates the advantage of using a $CO_2$-treated urea adduct (hereafter termed "recycled urea") such as is obtained in the method of this invention, in the urea fractionation step of a fish oil processing system.

The recycled urea used contained 3.5% fat.

Urea (80 g, recycled or in pellet form) in ethanol (88 g) was held at reflux temperature for 30 min. Fatty acid ethyl esters (40 g, 54% EPA+DHA) were added, and the solution held at reflux temperature for another 2 hours. Subsequent cooling of the solution to 10° C. caused precipitation of the urea adduct. The urea adduct was removed by filtration, and the product oil was recovered by evaporation of the solvent. The fatty acid composition of the product oil was determined by gas chromatography.

When using urea in pellet form, the concentration of EPA+DHA in the product oil was 76%. However, when using the recycled urea, the concentration of EPA+DHA in the product oil increased to 85%.

EXAMPLE 4

Urea adduct with 26% fatty acid ethyl esters was treated. The concentration of EPA+DHA in the fat was 18%.

Step 1: Urea adduct (3.0 kg) was treated with supercritical $CO_2$ at 300 bar and 50° C. The $CO_2$-consumption was 8 kg/kg feed. 0.10 kg fatty acid ethyl esters were extracted (13% of theoretical yield of fat). The concentration of EPA+DHA in the product was 67%.

Step 2: The urea adduct from Step 1 was treated further with supercritical $CO_2$ at 400 bar and 80° C. The $CO_2$-consumption in this step was 17 kg/kg feed.

0.64 kg fatty acid ethyl esters were extracted (82% of theoretical yield of fat). The concentration of EPA+DHA in the product was 10%.

EXAMPLE 5

Urea adduct with 29% fatty acid ethyl esters was treated. The concentration of EPA+DHA in the fat was 58%.

Step 1: Urea adduct (3.0 kg) was treated with supercritical $CO_2$ at 300 bar and 500° C. The $CO_2$-consumption was 7 kg/kg feed. 0.37 kg fatty acid ethyl esters were extracted (43% of theoretical yield of fat). The concentration of EPA+DHA in the product was 73%.

Step 2: The urea adduct from Step 1 was treated further with supercritical $CO_2$ at 400 bar and 80° C. The $CO_2$-consumption in this step was 11 kg/kg feed.

0.49 kg fatty acid ethyl esters were extracted (56% of theoretical yield of fat). The concentration of EPA+DHA in the product was 42%.

EXAMPLE 6

Urea adduct with 29% fatty acid ethyl esters was treated. The concentration of EPA+DHA in the fat was 58%.

Step 1: Urea adduct (80 g) was treated with supercritical $CO_2$ at 250 bar and 50° C. for 30 min. $CO_2$ flow rate was 2.0 kg/hr. 10.7 g fatty acid ethyl esters were extracted (46% of theoretical yield of fat). The concentration of EPA+DHA in the product was 73%.

When performing the extraction at 60° C. instead of 50° C., other conditions remaining the same, the amount of fat extracted increased to 51% of theoretical yield, but the concentration of EPA+DHA in the product decreased to 67%.

What is claimed is:

1. A method for recovering polyunsaturated fatty acids or fatty acid esters or fatty acid amides from a urea adduct containing saturated and/or monosaturated fatty acids, esters or amides in addition to polyunsaturated fatty acids, esters or amides which method comprises the steps of:
   a) subjecting said urea adduct to extraction treatment with a subcritical or supercritical fluid at temperature not above 70° C., and
   b) recovering from said fluid a fatty acid fraction enriched in said polyunsaturated fatty acids.

2. A method according to claim 1, wherein said extraction treatment is effected with a supercritical fluid.

3. A method according to claim 2, wherein said extraction treatment is conducted at a temperature of from 40°–55° C.

4. A method according to claim 1, 2, or 3, wherein said urea adduct which has been subjected to said extraction treatment is then subjected to a further extraction treatment with a supercritical fluid at a temperature between 65° and 130° C.

5. A method according to claim 4, wherein said further extraction treatment is conducted at a temperature of from 70°–110° C.

6. A method according to claim 2, or 3, wherein said supercritical fluid is $CO_2$.

7. A method according to claim 1, 2, or 3, wherein said urea adduct is a by-product in a method of processing fish oil and contains EPA and/or DHA, and there is recovered from said supercritical fluid a fatty acid fraction enriched in said EPA and/or DHA.

8. A method according to claim 7, wherein said recovered fatty acid is recycled to said method of processing fish oil.

9. A method according to claim 1, 2, or 3, wherein said fatty acid fraction enriched in said polyunsaturated fatty acids is recovered from said supercritical fluid by reducing the pressure of said supercritical fluid below its critical pressure.

10. A method according to claim 4, wherein said urea adduct which has been subject to said further extraction treatment is recycled to a urea fractionating step in said method of processing fish oil.

11. A method according to claim 4, wherein said supercritical fluid used in both extraction treatments is $CO_2$.

12. A method according to claim 11, wherein said further extraction treatment is conducted at a temperature of from 70°–110° C.

13. A method according to claim 4, wherein said urea adduct is a by-product in a method of processing fish oil and contains EPA and/or DHA, and there is recovered from said supercritical fluid a fatty acid fraction enriched in said EPA and/or DHA.

14. A method according to claim 11, wherein said urea adduct is a by-product in a method of processing fish oil and contains EPA and/or DHA, and there is recovered from said supercritical fluid a fatty acid fraction enriched in said EPA and/or DHA.

15. A method according to claim 14, wherein said further extraction treatment is conducted at a temperature of from 70°–110° C.

16. A method according to claim 4, wherein said fatty acid fraction enriched in said polyunsaturated fatty acids is recovered from said superficial fluid by reducing the pressure of said supercritical fluid below its critical pressure.

17. A method according to claim 16, wherein said further extraction treatment is conducted at a temperature of from 70°–110° C.

18. A method according to claim 17, wherein said supercritical fluid is $CO_2$.

19. A method according to claim 18, wherein said urea adduct is a by-product in a method of processing fish oil and contains EPA and/or DHA, and there is recovered from said supercritical fluid a fatty acid fraction enriched in said EPA and/or DHA.

20. A method according to claim 19, wherein said recovered fatty acid fraction is recycled to said method of processing fish oil.

21. A method according to claim 13, wherein said urea adduct which has been subjected to said further extraction treatment is recycled to a urea fractionating step in said method of processing fish oil.

* * * * *

UNITED STATES PATENT AND TRADEMARK OFFICE
CERTIFICATE OF CORRECTION

PATENT NO. : 6,528,669 B1
DATED : March 4, 2003
INVENTOR(S) : Elin Kulås et al.

It is certified that error appears in the above-identified patent and that said Letters Patent is hereby corrected as shown below:

Title page,
Item [56], OTHER PUBLICATIONS, after "William Nilsson et al.:", "JACOCS," should read -- JAOCS, --; and after "M. Alkio, et al.:" "pp. 3," second occurrence, should be deleted.
Item [*] Notice, "0 days" should read -- 367 days --.
Item [57], ABSTRACT,
Line 3, "DPC 9/02," should be deleted.

Column 1,
Line 10, close up right margin.

Column 2,
Line 24, "is-employed" should read -- is employed --.
Line 29, "of-the" should read -- of the --.

Column 7,
Line 54, "500º C" should read -- 50º C --.

Column 8,
Line 40, "fatty acid" should read -- fatty acid fraction --.

Signed and Sealed this

Sixteenth Day of December, 2003

JAMES E. ROGAN
*Director of the United States Patent and Trademark Office*